United States Patent
Niiyama

(10) Patent No.: US 9,279,757 B2
(45) Date of Patent: Mar. 8, 2016

(54) BLOOD MEASURING APPARATUS

(75) Inventor: Yoshihiro Niiyama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 541 days.

(21) Appl. No.: 13/323,627

(22) Filed: Dec. 12, 2011

(65) Prior Publication Data

US 2012/0146619 A1    Jun. 14, 2012

(30) Foreign Application Priority Data

Dec. 13, 2010  (JP) ................. 2010-276908

(51) Int. Cl.
*G01N 27/00*  (2006.01)
*G01N 15/12*  (2006.01)
*G01N 15/06*  (2006.01)
*G01N 15/10*  (2006.01)

(52) U.S. Cl.
CPC ............ *G01N 15/12* (2013.01); *G01N 15/0656* (2013.01); *G01N 15/1056* (2013.01); *G01N 15/1218* (2013.01); *G01N 2015/1062* (2013.01)

(58) Field of Classification Search
CPC .............. G01N 15/12; G01N 15/1209; G01N 15/1218; G01N 15/1056; G01N 15/0656; G01N 2015/1062
USPC .......... 324/71.4; 210/645; 239/405; 73/865.5
See application file for complete search history.

(56) References Cited

U.S. PATENT DOCUMENTS

| | | | |
|---|---|---|---|
| 3,739,258 A * | 6/1973 | Karuhn et al. ............... | 324/71.1 |
| 4,137,168 A | 1/1979 | Perrot | |
| 4,253,058 A * | 2/1981 | Kachel et al. ................ | 324/71.1 |
| 4,351,731 A | 9/1982 | Perrot | |
| 4,473,185 A * | 9/1984 | Peterson et al. .................. | 239/8 |
| 4,710,021 A | 12/1987 | von Behrens | |
| 5,166,537 A | 11/1992 | Horiuchi et al. | |
| 5,266,269 A * | 11/1993 | Niiyama et al. ................ | 422/73 |

(Continued)

FOREIGN PATENT DOCUMENTS

| | | |
|---|---|---|
| CN | 1261957 A | 8/2000 |
| CN | 101165485 A | 4/2008 |

(Continued)

OTHER PUBLICATIONS

Japanese Office Action for the related Japanese Patent Application No. 2010-276908 dated Oct. 3, 2013.

(Continued)

*Primary Examiner* — Tung X Nguyen
*Assistant Examiner* — Adam Clarke
(74) *Attorney, Agent, or Firm* — Kenealy Vaidya LLP

(57) ABSTRACT

A blood measuring apparatus includes: a first chamber which includes a first wall provided with an aperture and in which diluted blood is contained; a second chamber which includes the first wall, a second wall opposed to the first wall and a peripheral wall and in which diluting solution is contained, the first and second chambers communicating with each other through the aperture; first and second electrodes which are disposed in the first and second chambers, respectively; a measuring unit which performs a blood measurement by causing a current to flow between the first and second electrodes; a diluting solution supplying unit which supplies diluting solution along a part of the peripheral wall which is adjacent to a peripheral edge of the first wall; and a sucking unit which sucks the diluting solution from the second wall.

6 Claims, 5 Drawing Sheets

(56) References Cited

U.S. PATENT DOCUMENTS

| | | | |
|---|---|---|---|
| RE36,074 E * | 2/1999 | Kouzuki | 324/71.4 |
| 6,098,471 A * | 8/2000 | Berndtsson et al. | 73/864.87 |
| 6,111,398 A | 8/2000 | Graham | |
| 6,417,658 B1 * | 7/2002 | Inami | 324/71.4 |
| 6,909,269 B2 * | 6/2005 | Nagai et al. | 324/71.4 |
| 8,771,484 B2 * | 7/2014 | Zhao et al. | 204/403.01 |
| 2008/0093216 A1 | 4/2008 | Zhao et al. | |
| 2008/0122423 A1 | 5/2008 | Luo et al. | |
| 2009/0031828 A1 | 2/2009 | Ulevicius et al. | |
| 2013/0345989 A1 * | 12/2013 | Miyamura | G01N 27/06 702/21 |
| 2015/0020613 A1 * | 1/2015 | Niiyama et al. | 73/863.21 |

FOREIGN PATENT DOCUMENTS

| | | |
|---|---|---|
| CN | 101173887 A | 5/2008 |
| CN | 101266205 A | 9/2008 |
| JP | 60-143742 A | 7/1985 |
| JP | 61-159134 A | 7/1986 |
| JP | 2815435 B2 | 10/1998 |
| JP | 2009-142748 A | 7/2009 |
| JP | 2010-125441 A | 6/2010 |
| WO | 2005/066610 A1 | 7/2005 |

OTHER PUBLICATIONS

Chinese Office Action for the related Chinese Patent Application No. 201110415456.0 dated Jan. 13, 2014.

The Extended European Search Report for the related European Patent Application No. 11193026.9 dated Jan. 2, 2013.

Office Action from Chinese Patent App. No. 201110415456.0 (Aug. 26, 2015) with English language translation.

* cited by examiner

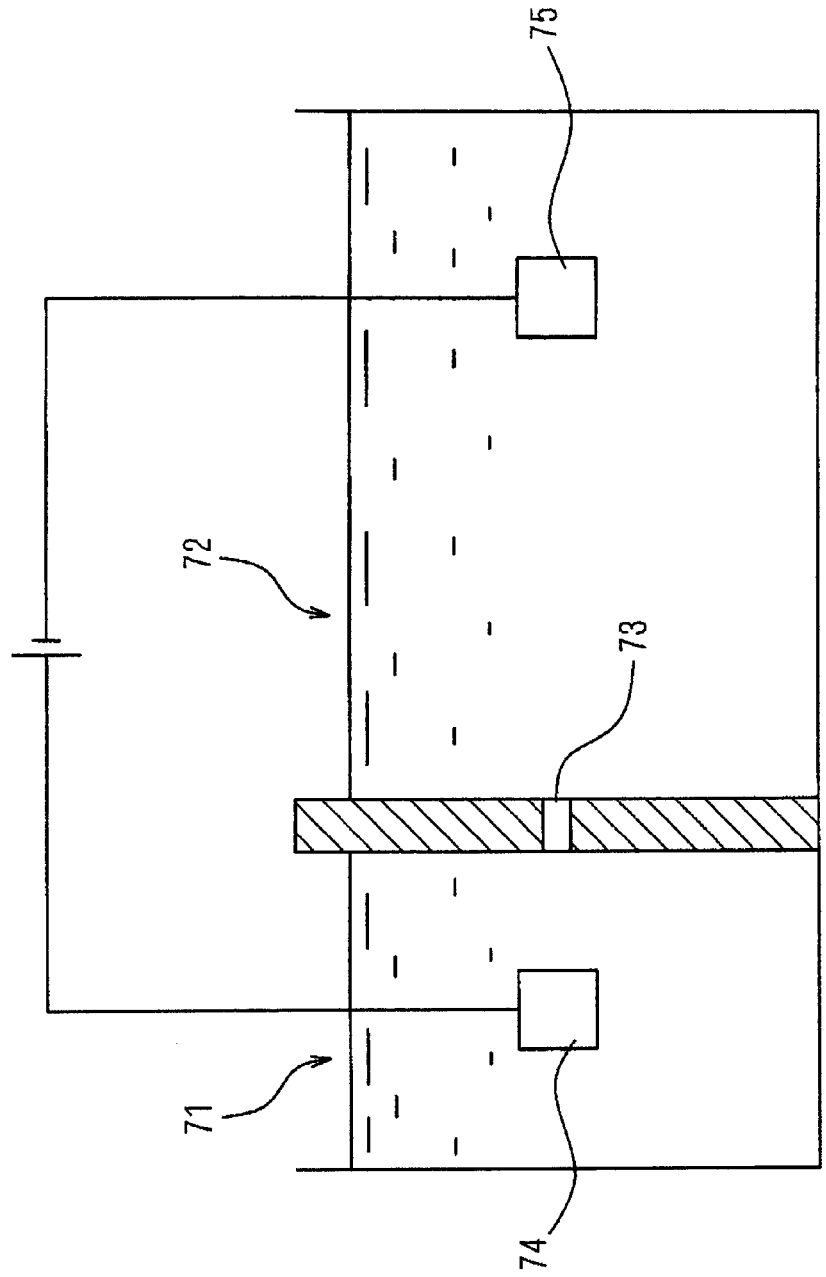

BLOOD MEASURING APPARATUS

BACKGROUND OF THE INVENTION

The present invention relates to a blood measuring apparatus which performs a blood measurement by using the electrical resistance method.

A related-art blood measuring apparatus is configured as shown in FIG. 5. An aperture 73 configured by a minute hole is disposed between a first chamber 71 and a second chamber 72. An electrode 74 is disposed in the first chamber 71, and an electrode 75 is disposed in the second chamber 72. Diluted blood is contained in the first chamber 71, and a diluting solution is contained in the second chamber 72.

In the related-art blood measuring apparatus in the above-described state, a minute current is caused to flow between the electrodes 74 and 75 through the aperture 73, a resistance change due to blood cells existing between the electrodes 74 and 75 is captured as a change in potential, and a blood measurement (blood cell count) is performed based on the potential change.

The diluted blood which flows from the first chamber 71 into the second chamber 72 through the aperture 73 is carried at an approximately constant distance after flowing into the second chamber 72, by a flow current which is directed toward the aperture 73, and then recirculates to the sensing region due to the electrodes 74 and 75. Therefore, recirculating blood cells exist in the sensing region, and hence it is impossible to capture a resistance change due to only blood cells passing through the aperture 73, so that there is a possibility that the counting operation is erroneously performed.

Moreover, a dead water region where liquid does not flow is produced in the vicinity of the aperture 73. Therefore, air bubbles adhere to a wall portion constituting the sensing region where the aperture 73 is included, and the adhering state of bubbles is varied by a pressure change or a change in liquid flowing state, thereby producing a problem in that such a variation may cause noises during the measurement.

As a related-art technique for, in the blood cell counting measurement, preventing a situation where an error is caused by re-detection due to vortex flow which is formed immediately after the passage through a minute hole, from occurring, there is the back sheath technique (see the right column of page 1 of JP-A-61-159134). When the technique is employed, however, the structure of an apparatus is complicated.

SUMMARY

It is therefore an object of the invention to provide a blood measuring apparatus in which blood cells that have passed through an aperture do not recirculate a sensing region, whereby an erroneous measurement can be prevented from occurring. It is another object of the invention to provide a blood measuring apparatus in which air bubbles hardly adhere to a wall portion constituting the sensing region where the aperture is included, and therefore noises are prevented from being produced during the measurement.

In order to achieve the object, according to the invention, there is provided a blood measuring apparatus comprising: a first chamber which includes a first wall provided with an aperture and in which diluted blood is contained; a second chamber which includes the first wall, a second wall opposed to the first wall and a peripheral wall and in which diluting solution is contained, the first and second chambers communicating with each other through the aperture; first and second electrodes which are disposed in the first and second chambers, respectively; a measuring unit which performs a blood measurement by causing a current to flow between the first and second electrodes; a diluting solution supplying unit which supplies diluting solution along a part of the peripheral wall which is adjacent to a peripheral edge of the first wall; and a sucking unit which sucks the diluting solution from the second wall.

The second chamber may have a cylindrical shape, the sucking unit may suck the diluting solution from a suction portion of the second wall, and a diameter of the suction portion of the second wall may be smaller than a diameter of the first wall.

A diameter of the peripheral wall may be gradually reduced as advancing from a predetermined portion toward the suction portion.

The diluting solution supplying unit may supply the diluting solution to generate a swirling flow.

BRIEF DESCRIPTION OF THE DRAWINGS

FIG. 5 is a schematic diagram illustrating a related-art blood measuring apparatus.

DETAILED DESCRIPTION OF EMBODIMENTS

Figure 1:
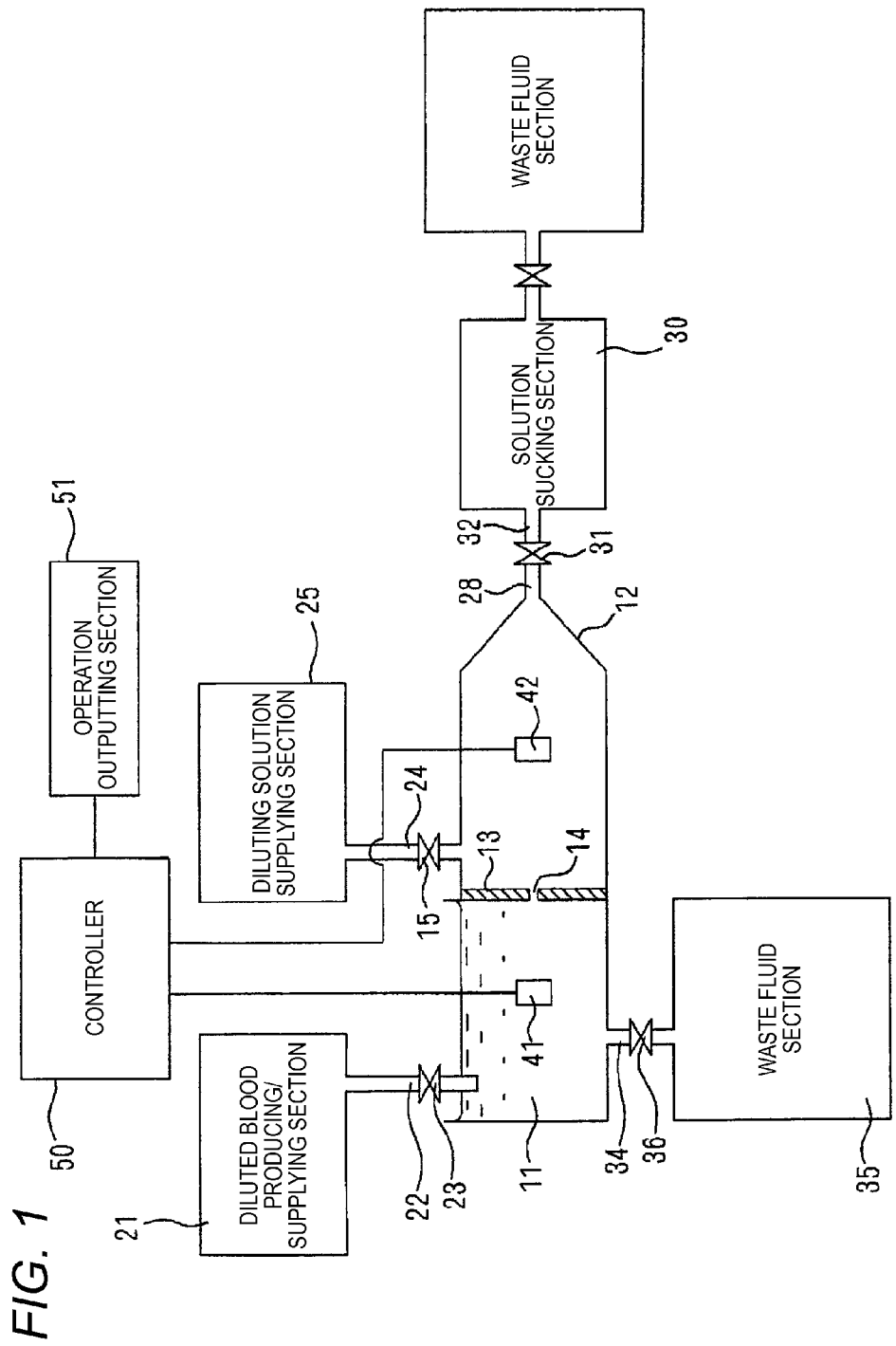
FIG. 1 is a diagram showing an embodiment of the blood measuring apparatus of the invention.

Hereinafter, an embodiment of the blood measuring apparatus of the invention will be described with reference to the accompanying drawings. In the figures, the identical components are denoted by the same reference numerals, and duplicate description will be omitted. FIG. 1 shows a block diagram of the embodiment of the blood measuring apparatus. The blood measuring apparatus includes a first chamber 11 and a second chamber 12. The first chamber 11 and the second chamber have a cylindrical (true cylindrical or elliptical cylindrical) shape in which the axis coincides with the lateral direction in the figure. The second chamber 12 is formed into a tapered shape in which the diameter is gradually reduced as advancing from a lateral approximately middle portion toward a right end portion.

A boundary wall 13 is vertically disposed between the first chamber 11 and the second chamber 12. An aperture 14 is formed in a middle portion of the boundary wall 13, and the first chamber 11 and the second chamber 12 communicate with each other through the aperture 14.

The first chamber 11 is connected to a diluted blood producing/supplying section 21. The diluted blood producing/supplying section 21 takes in sample blood by suction, dilutes the blood with a diluting solution (physiological saline or the like) to produce diluted blood, and supplies the diluted blood to the first chamber 11 through a pipe 22. A valve 23 is disposed in the pipe 22.

Figure 2:
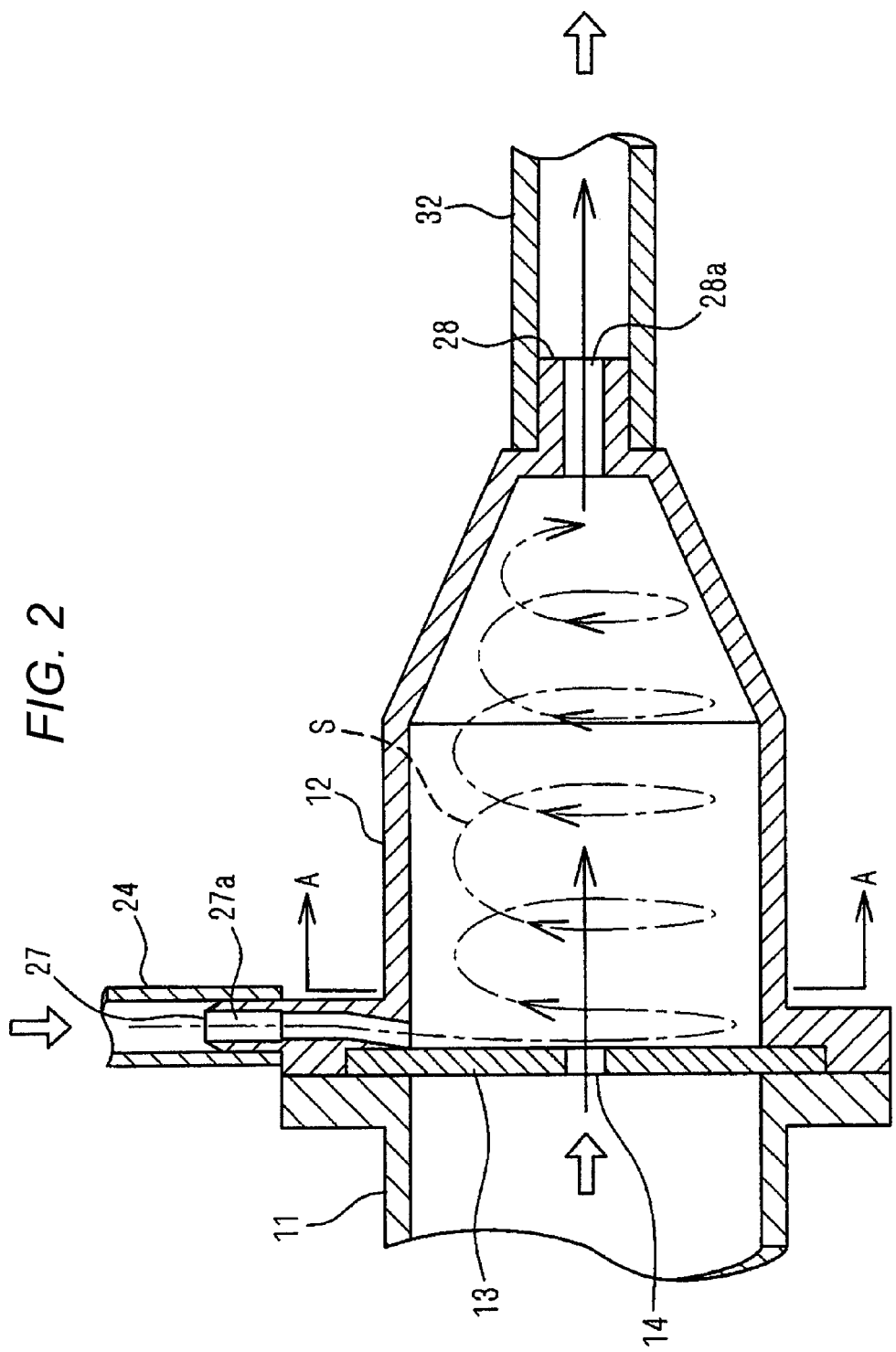
FIG. 2 is a longitudinal sectional view of a part of the embodiment of the blood measuring apparatus of the invention.
Figure 3:
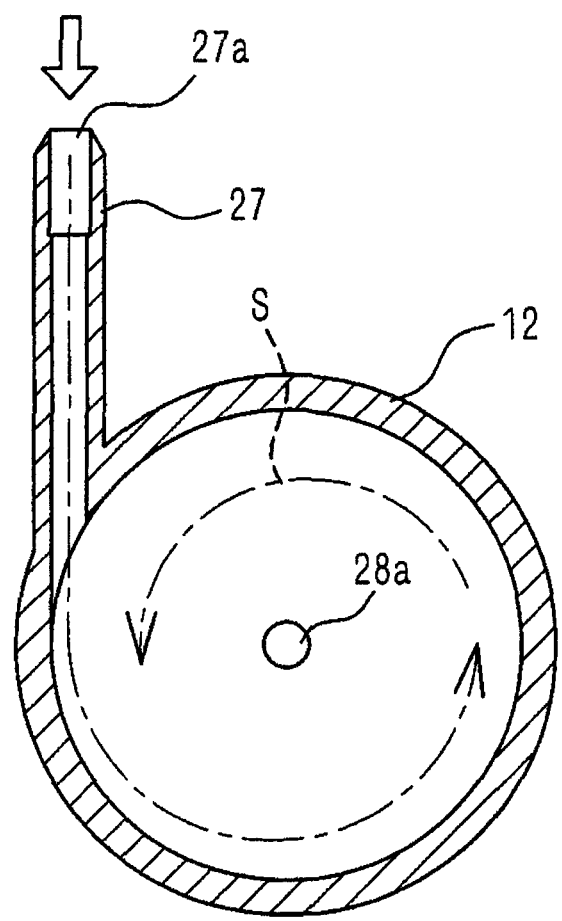
FIG. 3 is a sectional view taken along A-A in FIG. 2.

The second chamber 12 is connected to a diluting solution supplying section 25 through a pipe 24 in which a valve 15 is disposed. The diluting solution supplying section 25 stores the diluting solution. As shown in FIGS. 2 and 3, the pipe 24 is coupled with a fitting portion 27 which is disposed in the side wall of the second chamber 12. A flow path 27a in the fitting portion 27 extends toward the inner wall on the side of the second chamber 12 adjacent to the peripheral edge of the boundary wall 13.

The diluting solution supplying section 25 supplies the diluting solution by applying a predetermined pressure thereon. The supplied diluting solution flows in along the inner wall on the side of the second chamber 12 adjacent to the peripheral edge of the boundary wall 13 through the flow path 27a, and causes a swirling flow S to be produced in a situation where the second chamber 12 is filled with the diluting solution. In this way, the diluting solution supplying section 25 and the flow path 27a in the fitting portion 27 function as a diluting solution supplying unit which supplies the diluting solution along the inner wall on the side of the second chamber 12 adjacent to the peripheral edge of the boundary wall 13, thereby generating a swirling flow.

A fitting portion 28 which is straightly projected to the outside is disposed in an end portion of the second chamber 12 which is opposed to the boundary wall 13. An outlet 28a is formed in the fitting portion. The fitting portion 28 is connected to a solution sucking section 30 which constitutes a sucking unit, through a pipe 32 in which a valve 31 is disposed.

The solution sucking section 30 is configured by a suction pump and the like to suck the solution in the second chamber 12. Therefore, blood cells in the diluted blood which flows out from the aperture 14 to the side of the second chamber 12 are sucked into the solution sucking section 30 with maintaining a state where the blood cells are collected in the swirl center by the swirling flow that is produced as described above, and without being dispersed about the periphery and causing recirculation. The sucked solution is stored in a waste fluid section which is connected to the solution sucking section 30.

Figure 4:
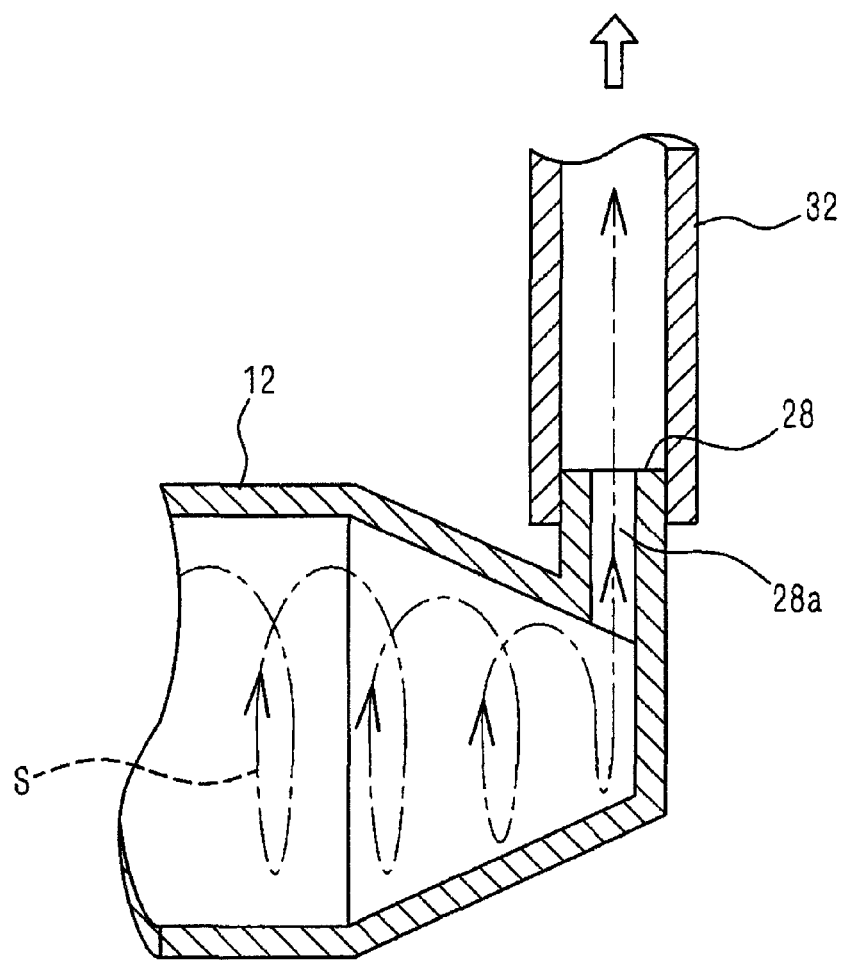
FIG. 4 is a longitudinal sectional view showing a modification of apart of the embodiment of the blood measuring apparatus of the invention.

FIG. 4 shows a modification of the fitting portion 28. In an end portion of the second chamber 12 which is opposed to the boundary wall 13, the fitting portion 28 is disposed to be upward projected in perpendicular to the wall of the end portion. The projection direction of the fitting portion 28 is not particularly limited.

A waste fluid section 35 is connected to the first chamber 11 through a pipe 34 in which a valve 36 is disposed. The waste fluid section 35 is configured by a tank which takes in the diluted blood in the first chamber 11, and which stores the diluted blood.

A first electrode 41 is disposed in the first chamber 11, and a second electrode 42 is disposed in the second chamber 12. The first electrode 41 and the second electrode 42 are opposed to each other across the aperture 14.

The first electrode 41 and the second electrode 42 are connected to a controller 50. The controller 50 is connected to an operation outputting section 51 having an outputting portion which displays or prints characters and the like, and an operating portion in which keys are disposed. The controller 50 controls the openings and closings of all the above-described valves, and functions as a measuring unit which sets a state where the diluted blood is contained in the first chamber 11, and the diluting solution is contained in the second chamber 12, and which causes a minute current to flow between the first and second electrodes 41 and 42 to perform a blood measurement.

The controller 50 captures a resistance change due to blood cells which are in the diluted blood, which flow from the first chamber 11 to the second chamber 12 through the aperture 14 and which exist between the first and second electrodes 41 and 42, as a change in potential, and performs a blood cell counting based on the change in potential. A result of the measurement is output from the operation outputting section 51.

During the measurement, the controller 50 opens the valve to supply the diluted blood from the diluted blood producing/supplying section 21, thereby controlling the diluted blood so as to flow from the first chamber 11 to the second chamber 12 through the aperture 14, and also opens the valve 15 to eject the diluting solution from the diluting solution supplying section 25 toward the inner wall on the side of the second chamber 12 adjacent to the peripheral edge of the boundary wall 13, through the flow path 27a in the fitting portion 27, thereby generating the swirling flow.

The swirling flow functions so as to collect the diluted blood which has flown to the side of the second chamber 12 through the aperture 14, toward the swirl center. At this time, the controller 50 opens the valve 31. Therefore, the solution sucking section 30 sucks the solution in the second chamber 12, and hence the diluted blood which is collected to the swirl center by the swirling flow is sucked into the solution sucking section 30 through the fitting portion 28 with maintaining a state where the diluted blood is collected in the swirl center. Consequently, the diluted blood which has flown out toward the second chamber 12 through the aperture 14 is formed into one stream which is partly slightly curved, and then directed toward the solution sucking section 30.

The process by the blood measuring apparatus of the embodiment is performed as described above. Therefore, blood cells can be prevented from recirculating to the sensing region, and an adequate measurement can be performed. Because of the swirling flow, air bubbles hardly adhere to the sensing region of the boundary wall 13, so that noises can be prevented from being produced, and a correct measurement can be performed.

According to an aspect of the invention, since the diluting solution is supplied along the inner wall on the side of the second chamber adjacent to the peripheral edge of the boundary wall, thereby causing a swirling flow, blood cells are surrounded by the swirling flow and are not dispersed. Since the diluting solution is sucked from the wall portion of the second chamber which is opposed to the aperture, the diluting solution is sucked in the sucking direction while the diluted blood is collected toward the swirl center by the swirling flow, whereby blood cells in the diluted blood are prevented from recirculating to the sensing region, so that a clean diluting solution always flows in the vicinity of the aperture. Therefore, it is possible to perform a correct measurement. Because of the swirling flow, moreover, air bubbles hardly adhere to the sensing region of the boundary wall. Therefore, noises can be prevented from being produced, and a correct measurement can be performed.

According to an aspect of the invention, since the second chamber has a cylindrical shape, the supplied diluting solution smoothly circulates along the circumferential wall of the cylinder, and the swirling flow can be adequately generated. Furthermore, the suction portion for the diluting solution has a diameter which is smaller than that of the boundary wall portion. Therefore, the diluted blood which is collected into the swirl center by the swirling flow is sucked while being accelerated.

According to an aspect of the invention, since the diameter of the second chamber is gradually reduced as advancing from the predetermined portion toward the suction portion for the diluting solution. Therefore, the diluted blood which is collected into the swirl center by the swirling flow is sucked while being accelerated, and a correct measurement can be performed.

What is claimed is:

1. A blood measuring apparatus comprising:
a first chamber which includes a first wall provided with an aperture and in which diluted blood is contained;
a second chamber which includes the first wall, a second wall opposed to the first wall and a peripheral wall and in which diluting solution is contained, the first and second chambers communicating with each other through the aperture;
first and second electrodes which are disposed in the first and second chambers, respectively;
a measuring unit which performs a blood measurement by causing a current to flow between the first and second electrodes;
a diluting solution supplying unit which supplies diluting solution along a part of the peripheral wall which is adjacent to a peripheral edge of the first wall; and
a sucking unit which sucks the diluting solution from the second wall,
wherein
the diluting solution supplying unit supplies the diluting solution to generate a swirling flow,
the swirling flow swirls so as to surround the diluted blood flowing into the second chamber, and
the swirling flow swirls about an axis extending from the first wall to the second wall.

2. The blood measuring apparatus according to claim 1, wherein the second chamber has a cylindrical shape, the sucking unit sucks the diluting solution from a suction portion of the second wall, and a diameter of the suction portion of the second wall is smaller than a diameter of the first wall.

3. The blood measuring apparatus according to claim 2, wherein a diameter of the peripheral wall is gradually reduced as advancing from a predetermined portion toward the suction portion.

4. The blood measuring apparatus according to claim 1, wherein the swirling flow has funneling motion.

5. The blood measuring apparatus according to claim 1, wherein the swirling flow has vortex motion.

6. The blood measuring apparatus according to claim 1, wherein the swirling flow has a whirlpool motion.

* * * * *